United States Patent [19]

Hernandez

[11] Patent Number: 5,148,032
[45] Date of Patent: Sep. 15, 1992

[54] RADIATION EMITTING DEVICE WITH MOVEABLE APERTURE PLATE

[75] Inventor: Fancisco Hernandez, Concord, Calif.

[73] Assignee: Siemens Medical Laboratories, Inc., Concord, Calif.

[21] Appl. No.: 723,000

[22] Filed: Jun. 28, 1991

[51] Int. Cl.[5] .............................................. G21F 5/04
[52] U.S. Cl. ................................ 250/492.1; 378/108; 378/151
[58] Field of Search ............... 250/492.1, 492.3, 505.1; 378/65, 152, 159, 64, 108, 109, 110, 111, 112, 151

[56] References Cited

U.S. PATENT DOCUMENTS

| | | | |
|---|---|---|---|
| 3,947,689 | 3/1976 | Wagner | 378/151 |
| 4,121,109 | 10/1978 | Taumann et al. | 250/505 |
| 4,137,460 | 1/1979 | Fitzsimmons et al. | 378/151 |
| 4,606,062 | 8/1986 | Saito | 378/112 |
| 4,831,260 | 5/1989 | DiBianca | 378/151 |
| 4,935,446 | 6/1990 | Hefter et al. | 378/151 |
| 5,019,713 | 5/1991 | Schmidt | 250/492.3 |

OTHER PUBLICATIONS

"Automatic Variation of Field Size and Dose Rate in Radiation Therapy", Mantel et al., J. Radiation Oncology Biol. Phys., Jul.-Aug. 1977, vol. 2, No. 7 and 8, pp. 697-704.
"Wedge-Shaped dose distributions by computer-controlled collimator motion", Kijewski et al., Med. Phys. 5(5), Sep./Oct. 1978, pp. 426-429.
"Computer-controlled Radiation Therapy", Levene et al., Radiology 129, Dec. 1978, pp. 769-775.
"Dose Optimization With Computer-Controlled Gantry Rotation, Collimator Motion and Dose Rate Variation", Chin et al., J. Radiation Oncology Biol. Phys., vol. 9, No. 5, May 1983, pp. 723-729.
"A Primer on Theory and Operation of Linear Accelerators in Radiation Therapy", U.S. Department of Health and Human Services, Rockville, Md., Dec. 1981.
Medical Physics, vol. 5, No. 5, Sep./Oct. 1978, pp. 426-429, Am. Assoc. Phys. Med.; P. K. Kijewski et al.: "Wedge-shaped dose distributions by computer controlled collimator motion".

Primary Examiner—Jack I. Berman
Assistant Examiner—Kiet T. Nguyen
Attorney, Agent, or Firm—Lawrence C. Edelman

[57] ABSTRACT

In a radiation emitting device, particularly in a radiation therapy device, isodose curves are adjusted both by a moveable plate that is controlled during irradiation and by varying the dose rate of the radiation beam during irradiation. By superimposing the effects of moving the plate and varying the dose rate of the radiation beam, it is possible to vary the isodose curve in the object of irradiation, so that a wide range of variation in the possible isodose curves is obtained. If the plate is moved at a constant speed, e.g. various wedge-shaped isodose curves can be easily achieved.

5 Claims, 2 Drawing Sheets

RADIATION EMITTING DEVICE WITH MOVEABLE APERTURE PLATE

BACKGROUND OF THE INVENTION

1. Technical Field

The present invention relates to a radiation emitting device, and more particularly to a radiation therapy device comprising a radiation source and an aperture plate arrangement located between the radiation source and an object for defining a field of radiation.

2. Description of the Prior Art

Radiation emitting devices are generally known and used for instance as radiation therapy devices for the treatment of patients. A radiation therapy device generally comprises a gantry which can be swiveled around a horizontal axis of rotation in the course of a therapeutic treatment. A linear accelerator is located in the gantry for generating a high energy radiation beam for therapy. This high energy radiation beam can be an electron radiation or photon radiation (X-rays) beam. During treatment, this radiation beam is trained on a zone of a patient lying in the isocenter of the gantry rotation. Such a radiation therapy device is described in greater detail in the publication "A Primer on Theory and Operation of Linear Accelerators in Radiation Therapy", U.S. Department of Health and Human Services, Rockville, MD, December 1981. In order to control the radiation emitted toward an object, an aperture plate arrangement is usually provided in the trajectory of the radiation beam between the radiation source and the object. For instance, a wedge-shaped energy dose distribution can be achieved by introducing a wedge-shaped absorption-filter between the radiation source and the object; however, in this case the filter has to be changed in accordance with each desired dose distribution. These dose distributions are commonly defined by isodose curves, measured in water.

It is also known to use a moveable aperture plate in connection with a constant radiation source as a substitute for a conventional wedge-shaped filter.

U.S. Pat. No. 4,121,109 discloses a radiation therapy device having a aperture plate arrangement in which at least one aperture plate is moveable. Further, from an article "Wedge-Shaped Dose Distribution by Computer-Controlled Collimator Motion" in Medical Physics (5), September/October 1978, pages 426 to 429, it is known to use a defined plate motion to obtain a wedge-shaped isodose curve during irradiation. Such a wedge shaped isodose curve is frequently desired in radiation therapy in order to adjust to the anatomical conditions of the treatment subject. The wedge-shaped isodose curve results from the fact that different areas of the radiation field are exposed to irradiation for varying lengths of time. The requisite motion of the plate is caused by an iterative process.

U.S. patent application Ser. No. 07/506,975 entitled "Radiation Therapy Device with Moveable Aperture Plates" by Ernst-Ludwig Schmidt and assigned to the same assignee to the present invention describes a radiation therapy device having an aperture plate arrangement in which at least one aperture plate is moveable and in which in the radiation path a non-moveable filter body is introduced, which has a decreasing absorptivity in the opening direction of the plate. By utilizing this non-moveable filter body, greater flexibility can be achieved in the isodose curves that are to be employed. By this means, it is possible to obtain an isodose curve which, for example, increases in the area to be investigated and then decreases again.

Unlike arrangements which have only an exchangeable absorption-filter body and no moveable plate arrangement, a wide variation in the isodose curves can be obtained with plate arrangements using moveable plates. However, such moving plates are rather heavy and therefore sophisticated motor control systems and motors are necessary for moving the plates according to given accurate speed profiles. Furthermore, since radiation is absorbed in the filter body, the efficiency of radiation use is reduced.

SUMMARY OF THE INVENTION

It is an object of the invention to provide a radiation emitting device which avoids the use of complicated speed profiles, and which nevertheless achieves various isodose curves that are to be employed.

According to the invention, the radiation emitting device for irradiating an object with a radiation beam generated in a radiation source comprises an aperture plate arrangement which is located in the trajectory of the radiation beam between the radiation source and the object and which includes a plurality of plates for determining a radiation field at the object. A control unit is provided which is coupled to at least one of the plurality of plates for moving it during irradiation, and which is coupled to the radiation source for changing the dose rate of the radiation beam during irradiation in such a manner that a given dose distribution is obtained in the radiation field.

According to a preferred embodiment of the invention the plate speed is kept constant during the plate movement. In this case, the speed control is very simple.

The radiation emitting device according to the present invention may be combined with a dosimetry system which detects deviations from a predetermined dose distribution for controlling the radiation therapy device while the dose distribution is generated. This control can be based on the difference between a preset accumulated dose and an actual accumulated dose at every plate position.

The radiation emitting device is particularly embodied as a radiation therapy device. By using the invention, in case of a treatment interrupt, the treatment can be continued at the predetermined curve by a re-positioning of the plate to the location where the radiation was turned off.

Additional objects and features of the invention will be more readily appreciated and better understood by reference to the following detailed description which should be considered in conjunction with the drawings.

DESCRIPTION OF THE PREFERRED EMBODIMENT OF THE INVENTION

Figure 1:
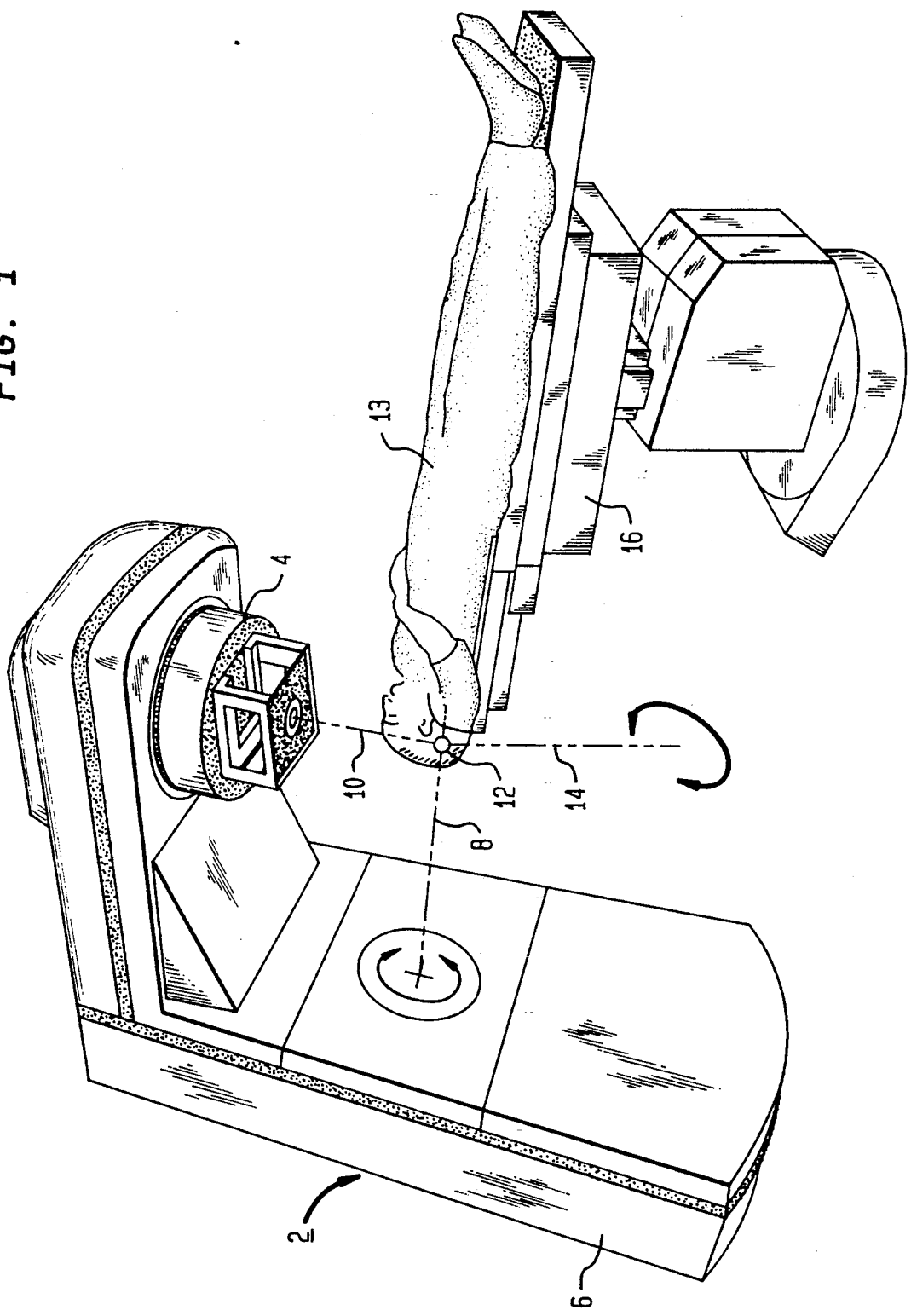
FIG. 1 shows a radiation therapy device including a plate arrangement and control unit constructed in accordance with the invention.

FIG. 1 shows a part of a radiation therapy device 2 of common design, in which plates 4 and a control unit 5 constructed in accordance with the principles of the invention are used. The radiation therapy device 2 comprises a gantry 6 which can be swiveled around a horizontal axis of rotation 8 in the course of a therapeutic treatment. The plates 4 are fastened to a projection of the gantry 6. To generate the high-powered radiation required for the therapy, a linear accelerator is located in the radiation therapy device 2. The axis of the radiation bundle emitted from the linear accelerator and the radiation therapy device 2 is designated by 10. Either electron radiation or photon radiation (X-ray radiation) can be used for the therapy. During the treatment, the radiation beam is trained on a zone 12 of a patient 13 which is to be treated and which lies in the isocenter of the gantry rotation. The rotational axis 8 of the gantry 6, the rotational axis 14 of a treatment table 16 and the beam axis 10 all intersect in the isocenter. The construction of such a radiation therapy device is described in detail in a publication "A Primer on Theory and Operation of Linear Accelerators in Radiation Therapy", U.S. Department of Health and Human Services, Rockville, MD, December 1981.

Figure 2:
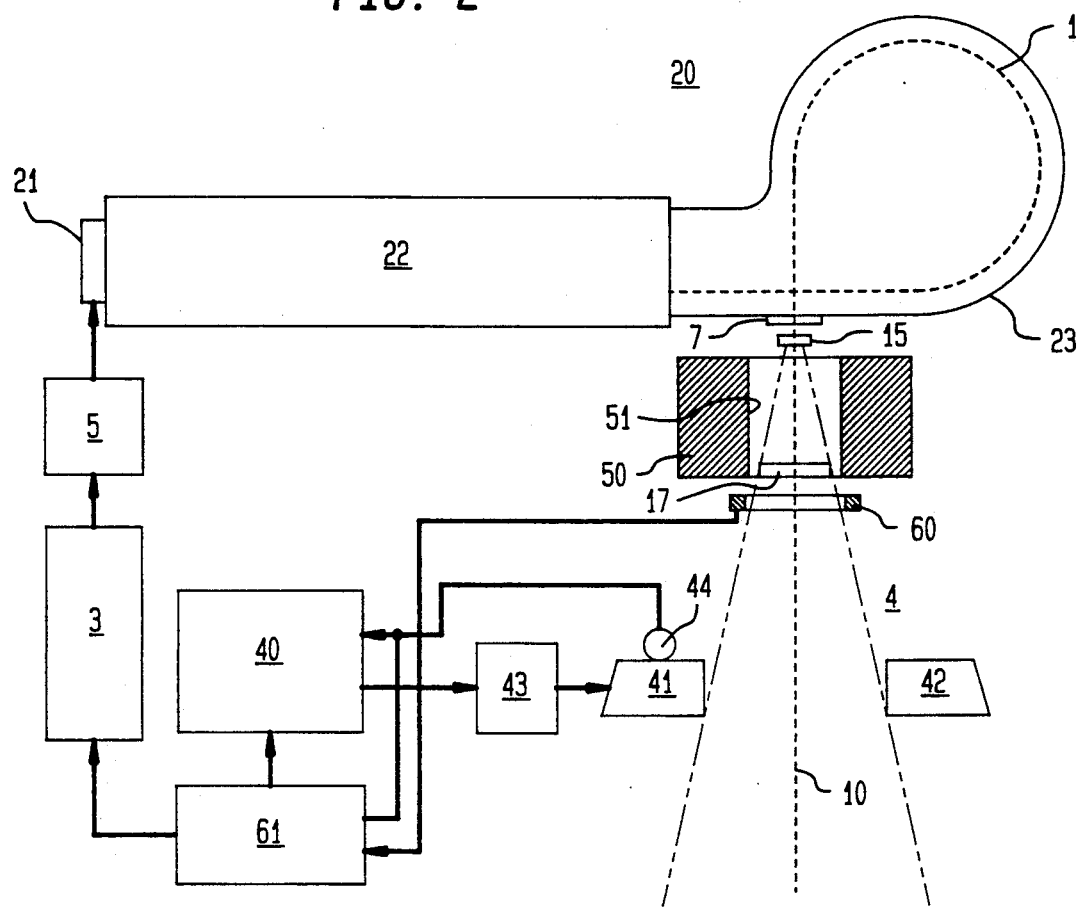
FIG. 2 illustrates portions of the control unit and beam generation system in the radiation therapy device according to FIG. 1.

FIG. 2 illustrates portions of the control unit and of the beam generation system in the radiation therapy device 2 according to FIG. 1. An electron beam 1 is generated in an electron accelerator 20. Accelerator 20 comprises an electron gun 21, a waveguide 22 and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating the electron beam 1. The electron beam 1 is accelerated and guided by waveguide 22. For this purpose, a HF source (not shown) is provided which supplies RF signals for the generation of an electromagnetic field supplied to waveguide 22. The electrons injected by injector 5 and emitted by electron gun 21 are accelerated by this electromagnetic field in waveguide 22 and exit at the end opposite to electron gun 21 as electron beam 1. Electron beam 1 then enters the guide magnet 23 which bends electron beam 1 by 270 degrees. Electron beam 1 then leaves guide magnet 23 through a window 7 along axis 10 and then encounters a first scattering foil 15, goes through a passage way 51 of a shield block 50 and encounters a second scattering foil 17. Next, it is sent through a measuring chamber 60, in which the dose is ascertained. If the scattering foils are replaced by a target, the radiation beam is a X-ray beam. Finally, aperture plate arrangement 4 is provided in the path of radiation beam 1, with which the irradiated field of the subject of investigation is determined. Aperture plate arrangement 4 comprises a pair of plates 41 and 42 which are moveable in a direction substantially perpendicular to axis 10 of radiation beam 1. An additional pair of aperture plates can be provided being moveable in a direction perpendicular to axis 10 and to the moving direction of plates 41 and 42. It is also possible that only one plate of said pair is moveable during radiation.

Plates 41 and 42 are moved by a drive unit 43 which is indicated only with respect to plate 41 in FIG. 2. Drive unit 43 comprises an electric motor which is coupled to plate 41 and which is controlled by a motor controller 40. A position sensor 44 is also coupled to plate 41 for sensing its position.

Motor controller 40 is coupled to a dose control unit which includes a dosimetry controller 61 for providing set values for the radiation beam dose rate in correlation with the position of plate 41 for achieving a given isodose curve. The dose rate of the radiation beam is measured by measuring chamber 60. In response to the deviation between the set values and the actual values, dosimetry controller 61 supplies signals to trigger system 3 which change the pulse repetition frequency so that the deviation between the set values and the actual values of the radiation beam dose rate is minimized. Thus, the dose control unit controls the dose rate of the radiation beam in correlation with the movement of plate 41 in order to achieve the given isodose curve. The ability to change the dose rate is generally known and it is particularly advantageous to use a digital dosimetry system.

Figure 3:
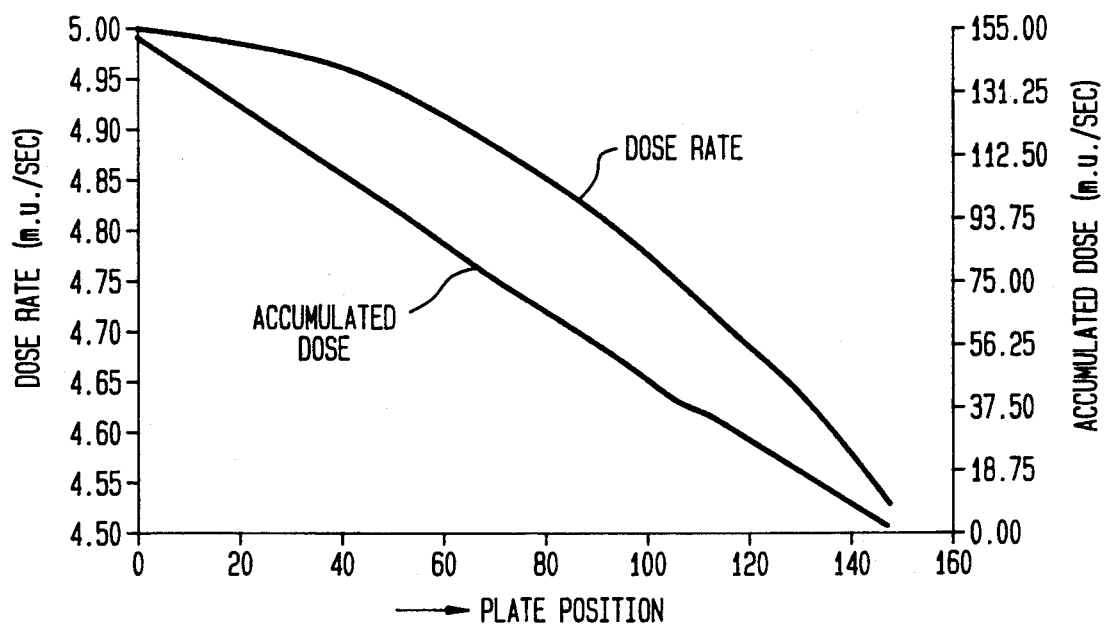
FIG. 3 shows a graph of the dose rate and the accumulated dose versus the position of one plate in the plate arrangement.

FIG. 3 shows a graph of dose rate and the accumulated dose for the radiation therapy device of FIGS. 1 and 2 with the moveable plate arrangement. During movement of the plate, the dose rate is changed in a way so that an accumulated dose is achieved which corresponds to a given rigid filter.

The mathematical algorithm for a dynamic wedge filter is as follows:

If one wants to generate a wedge-shaped isodose contour of an angle $\alpha$ at 10 cm depth, the dose profile at depth d can be expressed as:

$$D(d) = D_{surface} e^{-\bar{\mu} d} \quad (1)$$

wherein:

D(d) is the dose at depth d; and $\mu$ is the attenuation coefficient of the beam.

Assume we have a moving jaw at constant speed v along a radiation field of length $S_0$. Under the above conditions, it can be derived from equation (1) that the machine's intensity during the jaw movement should follow the function:

$$I\left(\frac{x}{v}\right) = \frac{v}{k} D_{10} \bar{\mu} tg\alpha \, e^{-\bar{\mu}(x - \frac{s_0}{2})tg\alpha}$$

and the total dose is:

$$D_{total} = \int_0^{\frac{s_0}{v}} I\left(\frac{x}{v}\right) d\left(\frac{x}{v}\right) + I_i t_i$$

wherein:

I is the machine's intensity;

x is the jaw position;

k is a scaling factor;

$D_{10}$ is the dose at the central axis 10 cm from the surface;

$\alpha$ is the desired wedge angle;

$I_1$ is the machine's constant intensity during the idle time;

$t_1$ is the idle time; and

D total is the total dose.

There has thus been shown and described a novel radiation therapy device which fulfills all the objects and advantages sought for. Many changes, modifications, variations and other uses and applications of the subject invention will, however, become apparent to those skilled in the art after considering the specification and the accompanying drawings which disclose an embodiment thereof. For example, the variation of the radiation dose rate does not have to be done simultaneously with the movement of the plates. The radiation could be interrupted or intermittently kept constant during the movement of the plates. All such changes, modifications, variations and other uses and applications which do not depart from the spirit and scope of the invention are deemed to be covered by the invention which is limited only by the claims which follow.

I claim:

1. A radiation emitting device for irradiating an object with a radiation beam, said radiation emitting device comprising:
    a radiation source for generating a radiation beam, said source including a pulse generating unit for generating pulses and wherein variation of the pulse repetition frequency of said pulses varies the dose rate of said radiation beam;
    an aperture plate arrangement located in the trajectory of said radiation beam between said radiation source and said object and including a plurality of plates for determining a radiation field at said object;
    a drive control unit coupled to said aperture plate arrangement for moving at least one plate of said plurality of plates at a constant speed;
    a dose rate measuring unit located in the trajectory of said radiation beam for measuring the dose rate of said radiation beam; and
    a dose control unit coupled to said radiation source, said dose rate measuring unit and to said drive control unit for varying the pulse repetition rate of said pulses, and hence the dose rate of said radiation beam during irradiation in correlation with the movement of said plate at constant speed.

2. The radiation emitting device according to claim 1, wherein:
    said dose rate controller includes means for providing preset values of dose rate for said radiation beam in correlation with movement of said at least one plate of said aperture plate arrangement.

3. The radiation emitting device according to claim 2, wherein:
    during movement of said aperture plate said dose rate control unit calculates the deviation between said preset values of dose rate and measured values of dose rate provided by said dose rate measuring unit, for providing a control signal to said pulse control unit which controls its pulse repetition frequency.

4. A radiation emitting device according to claim 3, wherein said pulse control unit generates trigger pulses, and wherein said dose control unit generates signals for varying the pulse repetition frequency of said trigger pulses in correlation with the movement of said plate.

5. A radiation emitting device according to claim 1, wherein said drive control unit comprises:
    a drive unit coupled to move said plate;
    a sensing device coupled to said plate for sensing its position; and
    a motor controller coupled to said drive unit and said sensing device for controlling the movement of said plate in a predetermined manner.

* * * * *